US00PP12794P2

(12) United States Plant Patent
Jones

(10) Patent No.: US PP12,794 P2
(45) Date of Patent: Jul. 23, 2002

(54) NEMESIA PLANT NAMED 'PENMYS'

(76) Inventor: Jimmy Jones, 14 Avondale Rd., Pontneywod Cumrangwent, S. Wales NP26 3AU (GB)

( * ) Notice: Subject to any disclaimer, the term of this patent is extended or adjusted under 35 U.S.C. 154(b) by 0 days.

(21) Appl. No.: 09/728,747

(22) Filed: Dec. 2, 2000

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Annette H. Para

(57) ABSTRACT

A new and distinct cultivar of Nemesia plant named 'Penmys' that is characterized by a profuse display of dark violet-blue flowers that are uniform, and a more compact form than others in this color range. In combination these characteristics set 'Penmys' apart from all other existing varieties of Nemesia known to the inventor.

3 Drawing Sheets

CROSS-REFERENCES TO RELATED APPLICATIONS

This application is related to another application entitled Nemesia Plant Named 'Pensug', having the same inventor as the present invention.

BACKGROUND OF THE INVENTION

The present invention relates to a new and distinct cultivar of Nemesia, that will be referred to hereinafter by the cultivar name 'Penmys'. The new Nemesia was selected in Netherwent, Caldicot, South Wales on May 1, 1998 by the inventor. The parents are of hybrid origin and have not themselves been released. The first crosses were made in 1997 with plants selected by the inventor from a long term Nemesia breeding program.

The breeding program involved cross-pollination of Nemesia hybrids from which seedling selection was based on the production of a dark blue flowering Nemesia, with numerous flowers, uniform flowers, and a compact habit.

The combined characteristics of the new invention 'Penmys' are unique. 'Penmys' is distinguished from other existing Nemesias by a compact habit, uniform flowers, and abundant flowers of a dark violet-blue color. The closest comparison cultivar is 'Woodcote' (unpatented), which is grown in the United Kingdom. 'Penmys' is distinguishable from 'Woodcote' (unpatented) by its greater abundance of flowers and its larger dimensions, 'Woodcote' (unpatented) being only 15 cm. tall when in full flower.

The new cultivar was first asexually propagated by the inventor on May 1, 1998 in Netherwent, Caldicot, South Wales, using terminal cuttings. 'Penmys' has been found to be true to type after many cycles of vegetative cuttings from 1998 to the present.

SUMMARY OF THE INVENTION

The following traits have been repeatedly observed and represent the distinguishing characteristics of the new invention. 'Penmys' is free-flowering, with dark violet-blue, uniform flowers and a more compact habit than other Nemesias in this color range. In combination these traits distinguish 'Penmys' from all other existing varieties of Nemesia known to the inventor.

BRIEF DESCRIPTION OF THE DRAWINGS

The accompanying color photographs illustrate the overall appearance of the new cultivar.

Sheet 1 illustrates the entire plant and habit.

Sheet 2 is a close-up view of the flowers.

Sheet 3 illustrates a stem with leaves and flowers. All photographs are taken of plants grown in two-gallon containers. The prints were made using conventional photographic techniques and although colors may appear different from actual colors due to light reflectance, they are as accurate as possible by conventional photography.

BOTANICAL DESCRIPTION OF THE PLANT

The following is a detailed description of the Nemesia cultivar named 'Penmys'. Data was collected in Arroyo Grande, Calif. from 9-month-old plants grown in two-gallon containers. Phenotypic differences may be observed with variations in environmental, climatic, and cultural conditions. The color determinations are in accordance with The Royal Horticultural Society Colour Chart except where general color terms of ordinary dictionary significance are used. The growing requirements are similar to other Nemesias and 'Penmys' is resistant to common pests and diseases.

Botanical classification: Nemesia hybrid.
Common name: Nemesia.
Use: Bedding and patio plant or hanging basket.
Parentage: Both parents are unnamed Nemesia hybrids.
Propagation: Tip cuttings.
Growth habit: Compact and mounding growth habit.
Form: Erect and upright.
Branching habit: Ascending, freely branching.
Plant dimensions: 54 cm. in height by 30 cm. in width.
Type: Vegetative annual.
Time to initiate roots: Approximately 16 days at temperatures of 21° Centigrade.
Time to develop roots: Approximately 28 days at temperatures of 21° Centigrade.
Rooting habit: Numerous and fine.
Vigor: Moderate.
Hardiness: USDA Zone 9.

Stem:
*Stem shape.*—Quadrilateral.
*Stem surface.*—Glabrous.
*Stem color.*—137C.
*Stem texture.*—Flexible with corner ridges and occasional flexuose stems.
*Internode length.*—4 cm. to 6 cm. between nodes.

Foliage:
*Leaf shape.*—Lanceolate.
*Leaf division.*—Simple.
*Apex.*—Acute.
*Base.*—Acuminate.
*Margins.*—Slightly serrate with rounded serrate tips.
*Texture.*—Flexible and glossy.
*Surface.*—Glabrous.
*Arrangement.*—Single, opposite and generally symmetrical.
*Lateral branch length.*—10 cm. in length.
*Lateral branch width.*—3 mm. in width.
*Number of leaves per lateral branch.*—Approximately nine leaves per lateral branch.
*Petiole length.*—Approximately 4 mm. in length.
*Petiole width.*—Approximately 1.5 mm. in width.
*Petiole color.*—137B.
*Leaf color upper surface* (*mature*).—139A.
*Leaf color lower surface* (*mature*).—137C.
*Leaf color upper surface* (*young*).—137B.
*Leaf color lower surface* (*young*).—138B.
*Venation upper surface.*—Three prominent and depressed.
*Venation lower surface.*—Three prominent and protruding.
*Vein color* (*upper surface*).—139A.
*Vein color* (*lower surface*).—137C.

Flowers:
*Flowering season.*—Spring through late autumn.
*Flowering time.*—Diurnal.
*Fragrance.*—Faint perfume scent.
*Self-cleaning or persistent.*—Self-cleaning.
*Flower length.*—2 cm. in length.
*Flower diameter.*—1.5–2 cm. in diameter.
*Type.*—Terminal inflorescence.
*Habit.*—Cluster.
*Quantity of flowers.*—Floriferous, approximately 10 to 12 flowers per terminal cluster.
*Petals.*—Four petals fused at base and basal fifth bi-labiate petal modified with nectar spur.
*Petal length.*—Fused petals are 1.2 cm. in length and fifth petal is 1 cm. in length.
*Petal width.*—Fused petals are 2 cm. in width and fifth petal is 1 cm. in width.
*Flower shape.*—Personate.
*Palate color.*—1A.
*Palate dimensions.*—3 mm. in length by 2 mm. in width.
*Surface.*—Smooth.
*Petal margin.*—Entire.
*Petal color* (*upper surface*).—90A and 88B.
*Petal color* (*lower surface*).—90D.
*Peduncle length.*—3 cm. in length.
*Peduncle width.*—1 mm. in width.
*Peduncle surface.*—Stipitate glandular surface.
*Peduncle texture.*—Slender and flexible, while strong enough to hold flowers.
*Peduncle color.*—138A.
*Calyx shape.*—Five-lobed.
*Calyx length.*—Approximately 3 mm. in length.
*Calyx diameter.*—Approximately 6 mm. in diameter.
*Sepal shape.*—Linear.
*Sepal apex.*—Acute.
*Sepal margin.*—Entire.
*Sepal surface.*—Stipitate glandular.
*Sepal color.*—Upper and lower surfaces 139B.
*Flower longevity.*—Flowers last 2–3 weeks.

Reproductive organs (Androecium) visible when retracting palate:
*Stamen number.*—Two in number.
*Anther size.*—Less than 0.5 mm. in length and width.
*Anther color.*—1A.
*Pollen color.*—1A.
*Amount of pollen.*—Low.

Reproductive organs (Gynoecium) visible when retracting palate:
*Pistil color.*—149D.
*Style length.*—Approximately 5 mm. in length.

Seed production:
*Quantity of seed.*—15 fertile seeds per capsule.
*Quantity of capsules.*—20 per flowering spike.
*Capsule dimensions.*—12 mm. in length and 7 mm. in width.
*Capsule color.*—177D.
*Capsule surface.*—Glossy.
*Appearance of seed.*—Flattened and winged.
*Seed color.*—200D and wing 156D.
*Shape of seed.*—Oval.
*Seed dimensions.*—3 mm. in length and 2.5 mm. in width.

I claim:

1. A new and distinct cultivar of Nemesia plant named 'Penmys' as described and illustrated.

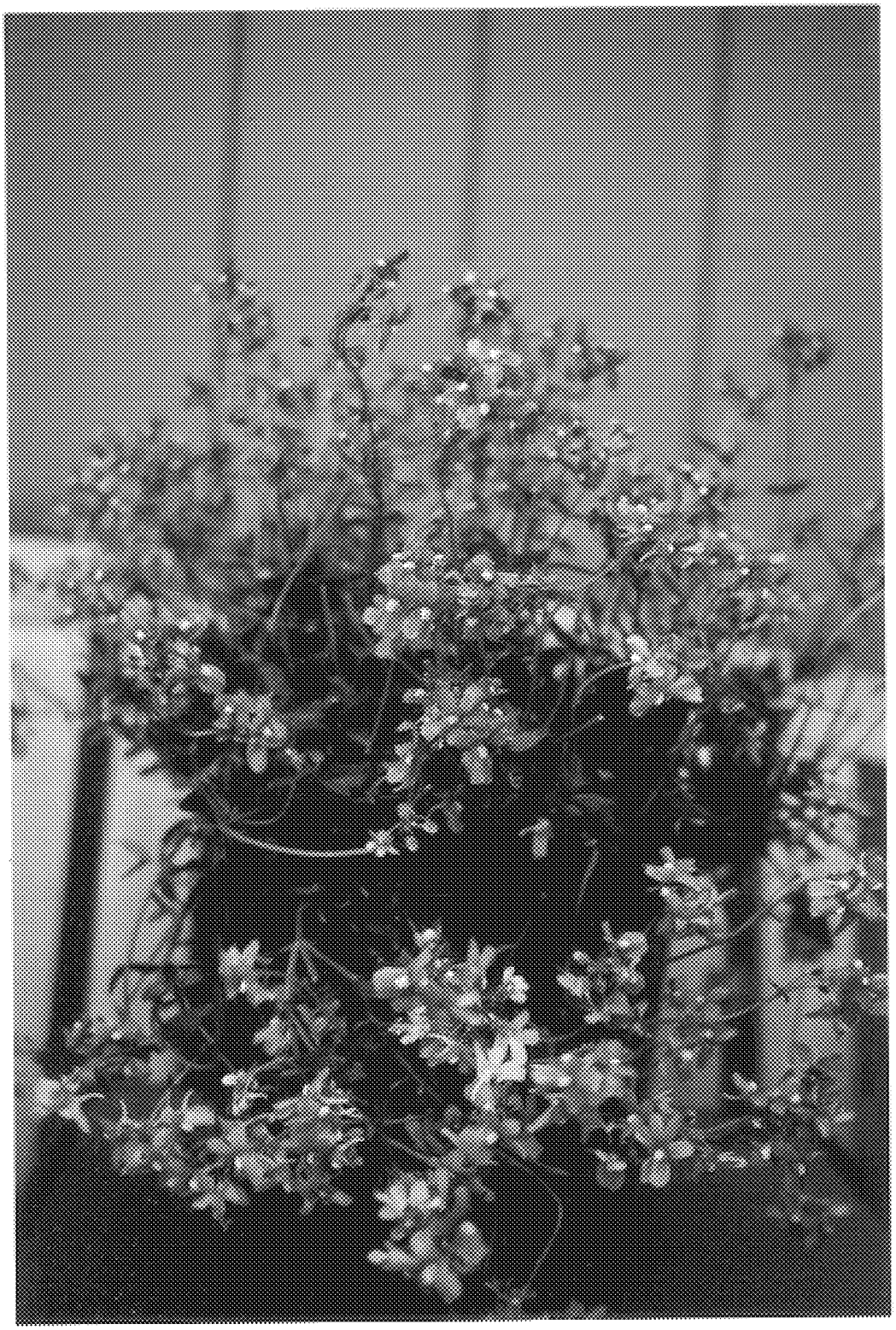

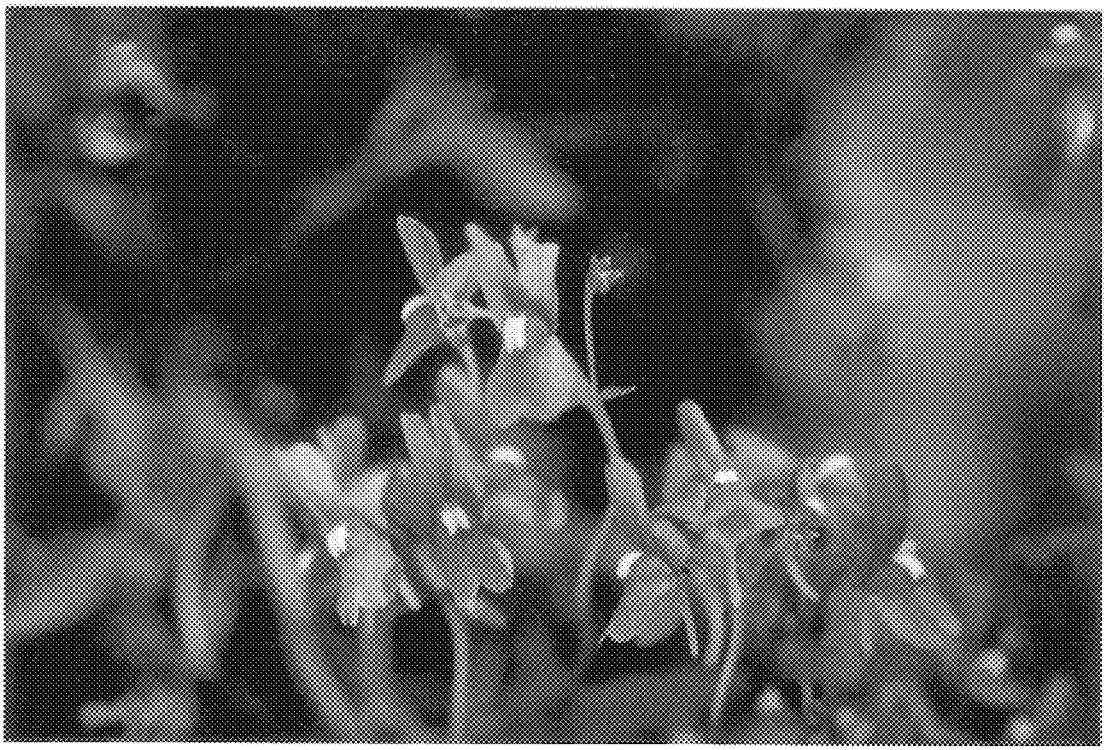

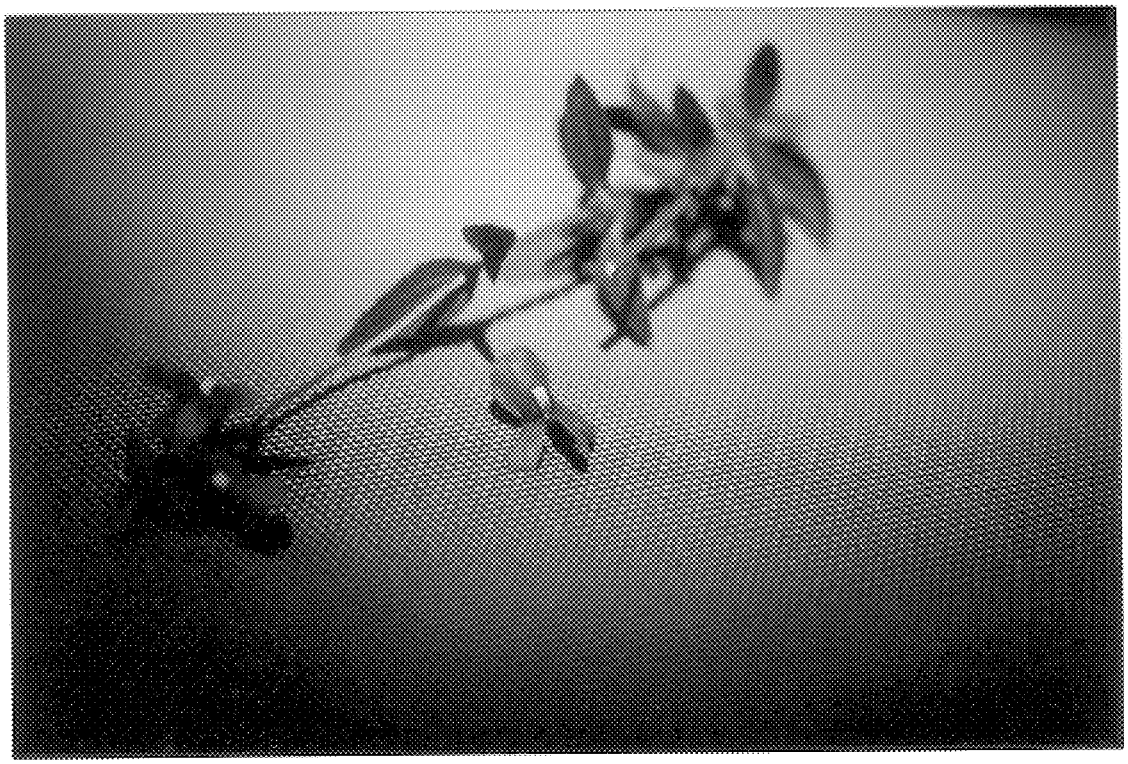

* * * * *